(12) United States Patent
Srivastava et al.

(10) Patent No.: US 8,063,217 B2
(45) Date of Patent: Nov. 22, 2011

(54) PROCESS FOR PREPARATION OF METHYL-(+)-(S)-ALPHA-(2-CHLOROPHENYL)-6, 7-DIHYDROTHIENO[3,2-C]PYRIDINE-5(4H) - ACETIC ACID METHYL ESTER OR SALTS THEREOF HAVING HIGHER CHIRAL PURITY AND PRODUCTS THEREOF

(75) Inventors: Anita Ranjan Srivastava, Maharashtra (IN); Prashant Pandurang Pawar, Maharashtra (IN); Krishna Anand Poojari, Maharashtra (IN); Pravin Chaitram Patil, Maharashtra (IN); Rajiv Ramchandra Dalvi, Maharashtra (IN)

(73) Assignee: RPG Life Sciences Limited, Mumbai, Maharashtra (IN)

( * ) Notice: Subject to any disclaimer, the term of this patent is extended or adjusted under 35 U.S.C. 154(b) by 667 days.

(21) Appl. No.: 11/993,249

(22) PCT Filed: Jul. 7, 2006

(86) PCT No.: PCT/IN2006/000250
§ 371 (c)(1),
(2), (4) Date: Dec. 20, 2007

(87) PCT Pub. No.: WO2007/032023
PCT Pub. Date: Mar. 22, 2007

(65) Prior Publication Data
US 2010/0004453 A1 Jan. 7, 2010

(30) Foreign Application Priority Data
Jul. 12, 2005 (IN) .............................. 836/MUM/2005
Jul. 6, 2006 (IN) .............................. 836/MUM/2006

(51) Int. Cl.
*C07D 513/02* (2006.01)
(52) U.S. Cl. ...................................................... 546/114
(58) Field of Classification Search ................... 546/114
See application file for complete search history.

(56) References Cited

U.S. PATENT DOCUMENTS

| | | | |
|---|---|---|---|
| 4,529,596 A | 7/1985 | Aubert et al. | |
| 4,847,265 A | 7/1989 | Badore et al. | |
| 5,132,435 A | 7/1992 | Bousquet et al. | |
| 5,204,469 A | 4/1993 | Descamps et al. | |
| 2004/0260110 A1 | 12/2004 | Bousquet et al. | |

FOREIGN PATENT DOCUMENTS

| | | |
|---|---|---|
| EP | 0281459 | 9/1988 |
| EP | 0465358 | 1/1992 |
| WO | 98/51682 A1 | 11/1998 |
| WO | 02/18357 | 3/2002 |
| WO | 02/18357 A1 | 3/2002 |
| WO | 2004/108665 | 12/2004 |
| WO | 2004/108665 A2 | 12/2004 |
| WO | 2005/003139 | 1/2005 |
| WO | WO 2005/003139 | * 1/2005 |

OTHER PUBLICATIONS

USP monograph 27NF22, IInd Supplement, effective from Aug. 1, 2004.
European Search Report: EP 06 83 2291.

* cited by examiner

*Primary Examiner* — Nizal Chandrakumar
(74) *Attorney, Agent, or Firm* — Ladas & Parry LLP

(57) ABSTRACT

A process for preparation of Methyl-(+)-(S)-alpha-(2-chlorophenyl)-6,7-dihydrothieno[3,2-c]pyridine-5(4H)-acetic acid methyl ester or salts thereof [clopidogrel or salts thereof of Formula (I)] having higher chiral purity and products thereof is provided. A process for purification of the compound prepared is also provided to enhance its efficacy by enhancing its optical rotation and chiral purity. In Formula (I), R is selected from a group comprising alkyl, alkoxy, hydroxy, amine etc., and $R_1$ is selected from the group comprising $C_{1-4}$ alkyl, $C_{1-4}$ alkoxy, hydroxy, nitro & halogen. The particular salt of interest of the present invention is the hydrogen sulfate of compound of the Formula (I), wherein R and $R_1$ are —$OCH_3$ and chloro-group at position 2 respectively.

(I)

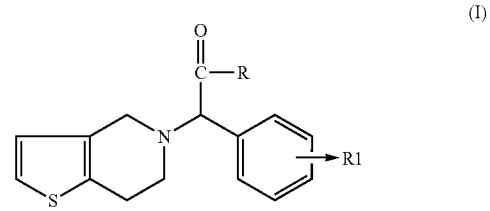

28 Claims, No Drawings

PROCESS FOR PREPARATION OF METHYL-(+)-(S)-ALPHA-(2-CHLOROPHENYL)-6,7-DIHYDROTHIENO[3,2-C]PYRIDINE-5(4H)-ACETIC ACID METHYL ESTER OR SALTS THEREOF HAVING HIGHER CHIRAL PURITY AND PRODUCTS THEREOF

TECHNICAL FIELD OF THE INVENTION

The present invention relates to a process for preparation of Methyl-(+)-(S)-alpha -(2-chlorophenyl)-6,7-dihydrothieno[3,2-c]pyridine-5 (4H) -acetic acid methyl ester or salts thereof having higher optical rotation of about 55.0 degree or more and higher chiral purity of about 99.0% or more and products thereof. Particularly, the present invention relates to a process for preparation of Methyl-(+)-(S)-alpha-(2-chlorophenyl)-6,7-dihydrothieno[3,2-c]pyridine -5(4H)-acetic acid methyl ester, commonly known as clopidogrel or salts thereof of Formula-I, which in-turn is purified to enhance its chiral purity and to the products prepared thereby.

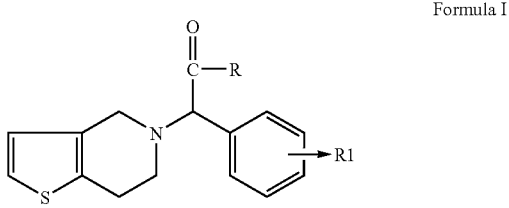

Formula I

In Formula-I, R is selected from a group comprising alkyl, alkoxy, hydroxy, amine etc., and $R_1$ is selected from the group comprising $C_{1-4}$ alkyl, $C_{1-4}$ alkoxy, hydroxy, nitro & halogen. The particular salt of interest of the present invention is the hydrogen sulfate of compound of the Formula-I, wherein R and $R_1$ are —$OCH_3$ and chloro-group at position 2 respectively.

BACKGROUND OF THE INVENTION

Clopidogrel and its hydrogen sulfate salt being chiral compounds, their S(+)enantiomer is a commercially significant drug reported to selectively interfere with Adenosine-Di-Phosphate (ADP) mediated platelet aggregation and cause an irreversible non-competitive inhibitor of platelet function with excellent anti-thrombotic activity. The dextrorotatory enantiomer bearing the international non-proprietary name (INN) Clopidogrel and its pharmaceutically acceptable salts have been disclosed in U.S. Pat. Nos. 4,847,265, 5,132,435, EP: 0281459, EP: 465358.

S(+)Clopidogrel hydrogen sulfate [may also be referred as S(+)Clopidogrel bisulfate has appeared in US Pharmacopoeia [USP]. According to USP monograph 27NF22, $II^{nd}$ Supplement, effective from 1, Aug. 2004, the minimum requirement of desired chiral purity of S(+)enantiomer is 99.0% by HPLC.

Generally the enantioselective-enriched compound can be prepared in two different ways. One is starting with enantioselective material and two is starting with racemic mixture following the resolution either at the intermediate stage or at the final stage.

The preparation from enantioselective-enriched compound is more preferred because it not only enhances yield of enantioselective-enriched end product, but also eliminates chances of impurity.

The preparation from racemic mixture to a racemic mixture of the end product followed by resolution to get enantioselective-enriched end product involves an additional step of resolution of racemic mixture of end product which in-turn reduces the yield of the desired end product. An attempt has been made to overcome the problem of yield by recycling the undesired intermediate after racemization, but these steps have been observed to increases the cost of production [WO2004/108665]. Further, it has been observed that the overall yield is not encouraging.

The preparation from racemic mixture to an enantioselective-enriched end product via resolution at the intermediate stage suffers from the problem of difficulty in isolation of the intermediate. In case the intermediate is resolved in-situ, then the yield of the process is quite low [U.S. Pat. No. 5,204,469].

Accordingly, the resolution techniques are associated with following limitations:
1. requirement of suitable resolving agents considered as chiral auxiliary;
2. recycling of resolving agents; and
3. isolation and racemization of undesired enantiomers.

Therefore, the preparation of the enantioselective-enriched compound is preferred from the enetioselective-enriched starting compound.

The U.S. Pat. No. 4,529,596 disclosed various derivatives of clopidogrel of Formula-I and their method of preparation. However, this patent disclosed the clopidogrel as racemic mixture of its enantiomers and no method of resolution has been disclosed. As per the processes of this patent esters of Formula I could be prepared by condensation of 4,5,6,7-tetrahydro-thieno[3,2-c]pyridine with an alpha-chlorophenyl acetate and amides of Formula I could be prepared by reacting an acid of formula (I)(R=OH) either with amine of formula $R_1$—NH—$R_2$ or with the alcohol of formula R—OH. In this patent, for the economic reasons, the reaction of acid of formula (I)(R=OH) with alcohol of formula R—OH was preferred as compared to other two alternatives. This method could also be employed for synthesis of certain higher esters of Formula I. The other two alternatives were held to be more uneconomical as compared to the reaction of acid of formula (I)(R=OH) with alcohol of formula R—OH. The preferred process has significant drawbacks when practiced on an industrial scale. For example, the alpha-halo-acetic acid derivatives used in the process are lachrymators and irritants and, therefore difficult in handling.

U.S. Pat. No. 4,847,265 discloses a method of resolution of racemic mixture of clopidogrel by forming a salt of the racemic mixture of clopidogrel with an optically active acid, preferably levo-rotatory camphor-10-sulfonic acid in an inert solvent. The main problem with this method is that the resolving agent employed, that is levo-rotatory camphor-10-sulphonic acid is expensive which enhances cost of production of enantiomeric clopidogrel. Another problem of this method is that the end product is prepared in very poor yield of about 50% due to formation of undesired levo-rotatory isomer of clopidogrel. Therefore, the attempt is to avoid the resolution of clopidogrel free base to get the desired end product —S(+) clopidogrel hydrogen sulfate.

U.S. Pat. No. 5,204,469 discloses that the clopidogrel of Formula-I can also be prepared by reacting methyl alpha-(2-thienylethylamino)(2-chlorophenyl)acetate, a compound of Formula-II with a formylating agent in presence of a solvent and then followed by cyclisation of the intermediate compound formed in the presence of an acid under anhydrous condition. The intermediate compound optionally could be isolated and then cyclised in the presence of an acid.

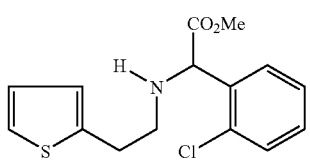

Formula II

The major problem of this process is that either it is a two step process requiring a step of formylation and then followed by a step of cyclisation or a three step process requiring a step of formylation, a step of isolation of intermediate and then followed by a step of cyclisation of the intermediate which has not been confirmed in this patent.

Further problem of this method is that whether a racemic mixture of compound of Formula II or a stereospecific compound of Formula II is taken as a starting material, the clopidogrel free base is isolated from the aqueous layer at a pH above 7 that is at an alkaline pH which is achieved by addition of sodium bicarbonate. It has been observed that when the clopidogrel free base is separated out at a basic pH, that is at a pH above 7, then it is obtained along with various chemical impurities which are very difficult to be separated out. Hence, this process cannot result in higher yield of clopidogrel free base of higher purity. The purity of clopidogrel free base may be increased, but by additional steps of repeated purification/recycling thereby making the process highly uneconomical.

Another problem of this process is that it requires anhydrous conditions to be maintained.

Still further problem of this process is that it requires additional organic solvents such as methylene chloride to dissolve dextrorotatory compound of Formula-II and anhydrous dimethylformamide containing hydrochloric acid for cyclisation of the intermediate prepared thereby resulting in further increase of cost of the process for preparation of dextrorotatory clopidogrel free base.

The S(+)clopidogrel hydrogen sulfate prepared by known methods is observed to have optical rotation of about 53 degree with chiral purity of less than about 98% as measured by HPLC. The requirement is to have S(+)clopidogrel hydrogen sulfate having optical rotation of about 55.0 degree or more with chiral purity of about 99.0% or more. The prior art does not teach how to enhance the optical rotation of S(+) clopidogrel hydrogen sulfate to have higher chiral purity, which is relatively more suitable as per US pharmacopeal requirement.

The another problem for preparing S(+)clopidogrel hydrogen sulfate having higher efficacy due to higher optical rotation with higher chiral purity from S(+)clopidogrel free base is that on reaction with conc. sulfuric acid, it results in formation of undesired clopidogrel hydrogen sulfate and other chemical impurities thereby does not result in preparation of S(+)clopidogrel hydrogen sulfate having desired optical rotation and chiral purity.

The another problem observed during purification of S(+) clopidogrel hydrogen sulfate having lower efficacy due to lower optical rotation and lower chiral purity to have S(+) clopidogrel hydrogen sulfate having higher efficacy due to higher optical rotation with higher chiral purity is that the undesired clopidogrel hydrogen sulfate [racemic and/or levorotatory] and other impurities also precipitate out along with desired S(+)clopidogrel hydrogen sulfate and further purification of such mass is very difficult to obtain desired S(+) clopidogrel hydrogen sulfate.

NEED OF THE INVENTION

Accordingly, there is a need to provide a method for preparing S(+)clopidogrel free base which can be directly converted to optically pure S(+)clopidogrel hydrogen sulfate. Further, there is a need to provide a method for preparing S(+)clopidogrel hydrogen sulfate from S(+)clopidogrel free base and to purify the same to provide S(+)clopidogrel hydrogen sulfate having higher optical rotation of about 55.0 degree or more, preferably about 55.5 degree or more with chiral purity about 99.0% or more, preferably about 99.5% or more.

OBJECTS OF THE INVENTION

The main object of the present invention is to provide a method for preparation of S(+)clopidogrel free base of Formula I from optically pure compound of Formula II to have S(+)clopidogrel free base having higher optical rotation with higher chiral purity.

The another object of the present invention is to provide a method for preparation of S(+)clopidogrel hydrogen sulfate of Formula I having higher optical rotation of about 55.0 degree or more, preferably about 55.5 degree or more with chiral purity about 99.0% or more, preferably about 99.5% or more directly from S(+)clopidogrel free base so as to avoid step of resolution at the end product stage thereby avoiding inherent problems of this step.

Another object of this invention is to provide a method for purification of S(+)clopidogrel hydrogen sulfate having lower optical rotation with lower chiral purity to provide S(+)clopidogrel hydrogen sulfate having higher optical rotation of about 55.0 degree or more, preferably about 55.5 degree or more with chiral purity about 99.0% or more, preferably about 99.5% or more.

This is another object of this invention to provide a process for preparation of optically pure clopidogrel free base which is not only one step process, but also less time consuming.

This is still an object of this invention to provide a process for preparation of optically pure clopidogrel free base wherein it can be isolated at a pH below 7 without any chemical impurities thereby resulting in highly pure optically active clopidogrel free base which in-turn can be converted to highly pure optically active clopidogrel hydrogen sulfate.

This is still another object of the present invention to provide a process for preparation of optically pure clopidogrel free base which avoids use of additional organic solvents thereby resulting in decrease in cost of production and making the process environment friendly.

Yet another object of this invention is to provide a process for enhancing optical rotation of S(+)clopidogrel hydrogen sulfate to about 55.0 degree or more, preferably 55.5 degree or more with chiral purity to about 99.0% or more, preferably about 99.5% or more thereby enhancing its efficacy to make it suitable as per US pharmacopeal requirements.

The other objects and advantages of the present invention will become apparent from reading of following description and examples.

BRIEF DESCRIPTION OF THE INVENTION

Accordingly, in one aspect [first embodiment] the present invention relates to a process for preparation of Methyl-(+)-(S)-alpha-(2-chlorophenyl) -6,7-dihydrothieno[3,2-c]pyridine-5(4H)-acetic acid methyl ester as free base [S(+)clopidogrel free base] of Formula-I:—

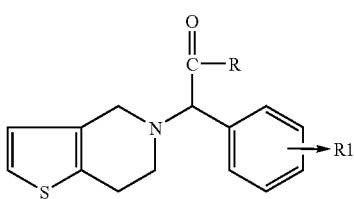

Formula-I comprising following steps:
a) reacting an aqueous solution of a S(+)enantiomer of compound of Formula-II as pharmaceutically acceptable acid addition salt, preferably as hydrochloride salt with paraformaldehyde and catalytic amount of hydrochloric acid;

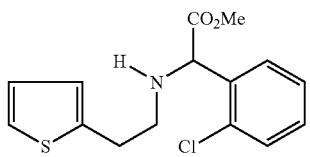

Formula II b) heating the reaction mixture of step a);
c) separating out the aqueous layer from the sticky mass;
d) extracting the S(+)clopidogrel free base from the aqueous layer obtained in step c) with petroleum ether or hexane while maintaining the pH varying between about 2 to about 3;
e) repeating the step d) while maintaining the said pH, varying between about 2 to about 3 of the aqueous layer; and
f) concentrating the combined organic layers obtained in steps d) and e) to result in S(+)clopidogrel free base in higher chemical purity and yield.

In another aspect [second embodiment] the present invention relates to a process for preparation of S(+)clopidogrel hydrogen sulfate having higher optical rotation of about 55.0 degree or more, preferably about 55.5 degree or more with chiral purity about 99.0% or more, preferably about 99.5% or more by stepwise reacting S(+)clopidogrel free base obtained in accordance with the method of the present invention with conc. sulfuric acid in presence of organic solvent and stepwise separating out S(+)clopidogrel hydrogen sulfate from the reaction mixture. It should be noted that presently disclosed process for preparation of S(+)clopidogrel hydrogen sulfate can also be employed on S(+)clopidogrel free base prepared in accordance with any known method. Accordingly, the second embodiment of the present invention is not restricted to the selection of S(+)clopidogrel free base of the present invention.

This is further aspect [third embodiment] of the present invention to provide a method for preparation of highly pure S(+)clopidogrel hydrogen sulfate having higher optical rotation of about 55.0 degree or more, preferably about 55.5 degree or more with chiral purity about 99.0% or more, preferably about 99.5% or more by dissolving S(+)clopidogrel hydrogen sulfate having lower optical rotation of about 53 degree in an organic solvent to have a clear solution followed by concentrating the solution and precipitating out the undesired clopidogrel hydrogen sulfate and other chemical impurities, if any by adding an anti-solvent. The undesired clopidogrel hydrogen sulfate and other chemical impurities are separated out as first lot solid and the filtrate is concentrated to dryness mixed with an organic solvent to give S(+)clopidogrel hydrogen sulfate having higher optical rotation of about 55.0 degree or more, preferably about 55.5 degree or more with chiral purity about 99.0% or more, preferably about 99.5% or more as a second lot solid.

It has been surprisingly observed that treatment of clear solution of S(+)clopidogrel hydrogen sulfate of lower optical rotation with lower chiral purity with an anti-solvent not only separates out undesired clopidogrel hydrogen sulfate and other chemical impurities, but also enhances the optical rotation and chiral purity of S(+)clopidogrel hydrogen sulfate to about 55.0 degree or more, preferably to about 55.5 degree or more and about 99.0% or more, preferably about 99.5% or more respectively.

The other objects and preferred embodiments and advantages of the present invention will become apparent from reading of following description and examples.

DETAILED DESCRIPTION OF THE INVENTION

I—Preparation of S(+)Clopidogrel Free Base:

In accordance with the first embodiment of the present invention, to a stirred aqueous solution of a S(+)enantiomer of compound of Formula-II as pharmaceutically acceptable acid addition salt, preferably as hydrochloride salt, paraformaldehyde and catalytic amount of mineral acid such as hydrochloric acid are added either simultaneously or one after other. The reaction mixture is stirred and heated at a temperature of about 75-85 degree C., preferably to about 75-80 degree C. for about 2 hours. During the reaction, the sticky mass separates out. The aqueous layer is separated out from the sticky mass and extracted with petroleum ether or hexane while maintaining the pH varying from about 2 to about 3 and the organic layer is collected. The step of extraction with petroleum ether or hexane is repeated for about two or three times while maintaining the said pH varying from about 2 to about 3 of the aqueous layer and the organic layers are collected. The said pH varying from about 2 to about 3 of the aqueous layer is maintained while extraction with the petroleum ether or hexane by addition of a base such as ammonia solution. The combined organic layers are concentrated and the clopidogrel free base is separated out in higher purity with good yield of the desired end product.

According to the presently disclosed process, paraformaldehyde is taken in an amount of about 12 to 18% of the amount of S(+)enantiomer of compound of Formula-II as pharmaceutically acceptable acid addition salt, preferably as hydrochloride salt and hydrochloric acid is taken in an amount of about 0.1 to 0.5% of the amount of S(+)enantiomer of compound of Formula-II as pharmaceutically acceptable acid addition salt, preferably as hydrochloride salt The use of hydrochloride salt of compound of Formula II as starting material results in use of reduced amount of the hydrochloric acid meaning thereby that no extra hydrochloric acid in stoichiometric amount or more is required for the preparation of clopidogrel free base.

It has been observed that generally acid salts break at the neutral pH of 7 to their free base. However, in the present case it has been surprisingly observed that clopidogrel hydrochloride salt prepared in the present method breaks to its free base at pH varying between about 3 or less and about 2 or more, that is varying from about 2 to about 3 of the aqueous layer.

It has been further observed that higher the pH, higher the impurities in the clopidogrel free base generated in the process and it is very difficult to separate out the chemical impurities from the clopidogrel free base to have better yield thereof with better purity. In present method, it has been surprisingly observed that when clopidogrel free base is extracted/separated out at lower pH and with petroleum ether or hexane the impurities are greatly reduced thereby resulting in preparation of clopidogrel free base of higher purity in higher yield. Therefore, in the present invention, the clopidogrel free base in higher yield having higher purity has been isolated/extracted from the aqueous layer with the help of petroleum ether or hexane while maintaining the pH varying from about 2 to about 3, preferably from about 2.2 to about 2.6 of the aqueous layer. After about two to three extractions of the aqueous layer with the petroleum ether or the hexane while maintaining the said pH varying from about 2 to about 3 of the aqueous layer, the combined organic layers are concentrated at a temperature of about 40 to 45 degree C. under a vacuum of about 400 to 600 mm to furnish the desired clopidogrel free base as colorless sticky liquid.

The yield of the free base has been observed to be 80% or more, preferably 85% or more making the process highly economical and the chemical purity as checked by Gas Chromatography has been found to be 99.5% or more, which meets the specific quality requirement.

It has been surprisingly observed that addition of catalytic amount of hydrochloric acid either along with paraformaldehyde or immediately after addition of paraformaldehyde results in direct cyclisation of the compound of Formula-II as its salt thereby resulting in saving on additional organic solvents to dissolve the compound of Formula II and to cyclise the intermediate formed during the process, and making the overall process highly economical and environment friendly. Accordingly, in accordance with preferred embodiment of the present invention, the catalytic amount of hydrochloric acid is added to a stirred aqueous solution of compound of Formula-II either along with paraformaldehyde or immediately after addition of paraformaldehyde.

Accordingly, the advantages of the present invention are that it provides a one step process to convert a stereospecific compound of Formula II as its salt to a stereospecific free base of Formula I without requiring preparation and isolation of any intermediate and the clopidogrel free base thus prepared is isolated at a pH varying between about 2 to about 3 to have the free base in higher yield of about 80% or more with higher chemical purity of about 99.5% or more.

II—Preparation of S(+)Clopidogrel Hydrogen Sulfate:

In accordance with second embodiment of the present invention, a process for preparation of S(+)clopidogrel hydrogen sulfate having higher optical rotation of about 55.0 degree or more, preferably about 55.5 degree or more with chiral purity of about 99.0% or more, preferably of about 99.5% or more by stepwise reacting S(+)clopidogrel free base with conc. sulfuric acid in presence of organic solvent and stepwise separating out S(+)clopidogrel hydrogen sulfate from the reaction mass is provided.

It has been surprisingly observed that when S(+)clopidogrel free base is reacted with conc. sulfuric acid in stepwise mode, in at least two steps, it results in removal of undesired clopidogrel hydrogen sulfate and other chemical impurities thereby resulting in preparation of S(+)clopidogrel hydrogen sulfate of desired optical rotation and chiral purity.

In accordance with one embodiment of the present invention, S(+)clopidogrel free base of Formula I is dissolved in mixture of organic solvents preferably a mixture of ketone and hydrocarbon, more preferably acetone and toluene followed by addition of first portion of one molar equivalent of conc. sulfuric acid which generates the undesired first lot material in 6-30% yield. After separation of the undesired first lot material, the balanced quantity of conc. sulfuric acid is added to the mother liquor to precipitate out the S(+)clopidogrel hydrogen sulfate of desired optical rotation and chiral purity.

According to present process about 2.2 to about 2.8 volumes of ketone are taken for each volume of S(+)clopidogrel free base of Formula I and about 0.2 to about 0.8 volumes of hydrocarbon are taken for each volume of S(+)clopidogrel free base of Formula I. The first portion of one molar equivalent of conc. sulfuric acid means about 5% to about 30% and second portion of conc. sulfuric acid means about 95% to about 70% of conc. sulfuric acid.

In accordance with one of the preferred embodiments of the present invention, the ketone may be methylethylketone, and hydrocarbon may be replaced with alcohol, preferably isopropyl alcohol or ether, preferably isopropylether. It has been observed that better results are achieved when the ketone is acetone and hydrocarbon is toluene. Therefore, acetone and toluene are more preferred solvents for this embodiment.

It has been observed that if the organic solvents mixture is replaced with mixture of alcohol and ester, preferably methanol and ethyl acetate, the conc. sulfuric acid can be added in one portion to separate out the undesired clopidogrel hydrogen sulfate in first lot and the desired S(+) clopidogrel hydrogen sulfate in second lot. Accordingly, in accordance with one embodiment of this invention, S(+)clopidogrel free base of Formula I is dissolved in mixture of alcohol and ester, preferably methanol and ethyl acetate followed by addition of one molar equivalent of conc. sulfuric acid resulting in separation of undesired first lot after a certain period of time, preferably 3-4 hrs. After separation of undesired first lot, the second lot of desired S(+)clopidogrel hydrogen sulfate is isolated from the mother liquor, which meets the requirement of optical rotation and chiral purity.

According to present invention, one volume of methanol is taken for each volume of S(+)clopidogrel free base of Formula I and one volume of ethyl acetate is taken for each volume of S(+)clopidogrel free base of Formula I which means that methanol and ethyl acetate are taken in a ratio of about 1:1. However, these may also be taken in a ratio varying from about 1:1 to about 1:2.

III—Purification of S(+)Clopidogrel Hydrogen Sulfate Salt:

In accordance with third embodiment of the present invention a method for preparation of highly pure S(+)clopidogrel hydrogen sulfate having optical rotation of about 55.0 or more, preferably of about 55.5 degree or more with chiral purity of about 99.0% or more, preferably of about 99.5% or more is provided.

Accordingly, in one embodiment the present invention also relates to a process for purification of S(+)clopidogrel hydrogen sulfate to enhance its efficacy by enhancing its optical rotation and chiral purity a) by dissolving S(+)clopidogrel hydrogen sulfate of lower optical rotation in an organic solvent to have a clear solution, b) concentrating the clear solution and adding about 1 volume of ester to precipitate out undesired clopidogrel hydrogen sulfate and chemical impurities which are separated out as first lot, c) followed by further concentration to dryness to give S(+)clopidogrel hydrogen sulfate of higher optical rotation and chiral purity as second lot on addition of organic solvent. The ester is preferably ethyl acetate, and organic solvents are preferably methanol and acetone.

In accordance with this invention S(+)clopidogrel hydrogen sulfate having lower optical rotation of about 53 degree is dissolved in methanol, preferably in 2 to 5 volumes of methanol to have a clear solution which is concentrated by reducing about 1 to 3 volumes of methanol. It may be noted that a care is taken that the volume of methanol is reduced to such an extent that the solution remains clear solution. To this clear concentrated solution about 1 volume of ester is added thereby precipitating out the undesired clopidogrel hydrogen sulfate and other chemical impurities, if any which are separated out as first lot which if desired can optionally be processed to separate out the S(+)clopidogrel hydrogen sulfate having lower optical rotation. The filtrate is concentrated to dryness and to the solid residue acetone is added and the second lot is filtered to give S(+)clopidogrel hydrogen sulfate having higher optical rotation of about 55.0 degree or more, preferably of about 55.5 degree or more with chiral purity of about 99.0% or more, preferably of about 99.5% or more.

It has been surprisingly observed that when an ester, preferably ethyl acetate is added to a clear solution of S(+)clopidogrel hydrogen sulfate in an organic solvent, preferably in alcohol, more preferably methanol, the undesired clopidogrel hydrogen sulfate [racemic and/or levo-rotatory] and other impurities, if any precipitate out first thereby resulting in a turbid solution which on filtration leaves behind the highly pure S(+)clopidogrel hydrogen sulfate, which is separated out in a second lot after separating out the first lot of precipitates of clopidogrel hydrogen sulfate. The optical rotation of S(+) clopidogrel hydrogen sulfate obtained in second lot has been observed to be about 55.0 degree or more, preferably about 55.5 degree or more with chiral purity of about 99.0% or more, preferably about 99.5% or more.

The organic solvent for dissolving S(+)clopidogrel hydrogen sulfate of lower optical rotation is alcohol, preferably methanol. The ester which is employed as an anti-solvent to precipitate out first lot of undesired clopidogrel hydrogen sulfate and other impurities is ethyl acetate.

The combined organic layer was concentrated at 40-45° C. under 400-600-mm vacuum to furnish the product as colorless sticky liquid. The yield of the end product was found to be 780 gm (83.57%). The chemical purity was checked by Gas Chromatography and found to be 99.90%.

Example-2

Preparation of Methyl-(+)-(S)-alpha-(2-chlorophenyl)-6,7-dihydrothieno[3,2-c]pyridine-5 (4H)-acetic acid methyl ester (Clopidogrel, Formula I) as hydrogen sulfate salt A solution of 100 gm of Methyl-(+)-(S)-alpha-(2-chlorophenyl)-6,7-dihydrothieno[3,2-c]pyridine-5(4H)-acetic acid methyl ester (Clopidogrel, Formula I) in a mixture of acetone (260 ml, 2.60 v) & toluene (40 ml, 0.4 v) was cooled to 9-10° C. The first portion of conc. sulfuric acid (98%) was added at 9-10° C. under stirring. After complete addition of sulfuric acid the reaction mixture was heated to room temperature 25-30° C. and stirred for 3 hrs. After 3 hrs the first lot solid was filtered and washed with 10 ml of acetone. The mother liquor was again cooled to 0-5° C. and second portion of conc. sulfuric acid (98%) was added at 0-5° C. under stirring. After complete addition of conc. sulfuric acid, the reaction mixture was heated to room temperature 25-30° C. and stirred for 3 hrs. The separated second lot solid was filtered and washed with 20-25 ml of acetone & dried at 40-45° C. for 3 hrs under 650-700 mm vacuum to furnish the final material.

The details are summarized in Table 1 as follows:

TABLE 1

| Sr. No. | Optical Rotation of Formula II as HCl salt | Percentage and Amount of conc. $H_2SO_4$ in gm | | | | Yield, Optical Rotation and Chiral HPLC of Formula I as hydrogen sulfate salt | | | | |
|---|---|---|---|---|---|---|---|---|---|---|
| | | Percentage | | Amount | | Yield | | Optical Rotation | | Chiral HPLC |
| | | I Lot | II Lot | I Lot | II Lot | I Lot | II Lot | I Lot | II Lot | II Lot |
| 1. | +80 to 85° | 30 | 70 | 9.34 | 21.76 | 36.0 | 80.0 | +15.3° | +55.9° | 99.77 |
| 2. | +99 to 103° | 12 | 88 | 3.73 | 27.37 | 14.3 | 103.1 | +16.1° | +56.2° | 99.79 |
| 3. | +104° to 106° | 10 | 90 | 3.10 | 28.00 | 11.80 | 106.0 | +22.2° | +55.8° | 99.80 |

1. Optical Rotation ($[\alpha]_D^{20}$) of Formula II was checked as HCl salt with 1.0% concentration of MeOH.
2. Optical Rotation ($[\alpha]_D^{20}$) of Formula I was checked as hydrogen sulfate salt with 2.0% concentration of MeOH The present invention will now be further elaborated with help of following examples which are not intended to limit scope of the present invention, however, have been incorporated merely to further illustrate the invention.

EXAMPLES

Example-1

Preparation of Methyl-(+)-(S)-alpha-(2-chlorophenyl)-6,7-dihydrothieno[3,2-c]pyridine-5(4H)-acetic acid methyl ester (Clopidogrel, Formula I)

To a stirred solution of (+)-methyl-alpha-(2-thienylethylamino)-N-(2-chlorophenyl) acetate as HCl salt of Formula II (1.0 kg) in water (5.0 L) was added para formaldehyde (130.24 gm) and 1.0 ml HCl at room temperature. The reaction mixture was stirred and heated to 78-80° C. for 2 hrs. The aqueous layer was first separated out from the sticky mass and extracted with petroleum ether (5.0 L) at pH 2.2-2.6. The aqueous layer was re-extracted with petroleum ether (3.0 L).

Example-3

Preparation of Methyl-(+)-(S)-alpha-(2-chlorophenyl)-6,7-dihydrothieno[3,2-c]pyridine-5 (4H)-acetic acid methyl ester (Clopidogrel, Formula I) as hydrogen sulfate salt 229 gm of Methyl-(+)-(S)-alpha-(2-chlorophenyl)-6,7-dihydrothieno[3,2-c]-pyridine-5(4H)-acetic acid methyl ester (Clopidogrel, Formula I) was dissolved in methanol (229 ml) and ethyl acetate (229 ml) was cooled to 0-5° C. To this solution conc. Sulfuric acid (98%, 71.30 gm) was added under stirring between 0-5° C. After complete addition reaction mixture was heated to room temperature 25-30° C. and stirred for 3 hrs. After 3 hrs the first lot of solid was filtered off and washed with 25 ml of acetone. The mother liquor was concentrated to dryness & to this residue 350.0-ml acetone was added. This reaction mixture was further stirred at room temperature for 4 hrs. The second lot solid was filtered & washed with 50 ml of acetone. The material was dried under vacuum at 40-45° C. for 3 hrs under 650-700 mm vacuum to furnish the final material.

The details are summarized in Table 2 as follows:

TABLE 2

| Isolated Material of Formula I as hydrogen | Yield | | Optical | Chiral HPLC Purity (%) of Formula I as hydrogen sulfate salt | |
|---|---|---|---|---|---|
| SN hydrogen sulfate salt | gm | % age | Rotation | S(+)Enantiomer | R(−)Enantiomer |
| 1. First Lot | 19.45 | 6.51 | +23.9° | 72.08 | 27.92 |
| 2. Second Lot | 242.0 | 80.94 | +56.1° | 99.61 | 00.39 |

Optical Rotation ($[\alpha]_D^{20}$) of Formula I is checked as hydrogen sulfate salt with 2.0% concentration of MeOH.

Example-4

Purification of Methyl-(+)-(S)-alpha-(2-chlorophenyl)-6,7-dihydrothieno[3,2-c]pyridine-5 (4H)-acetic acid methyl ester (Clopidogrel, Formula I) as hydrogen sulfate salt 500 gm of Methyl-(+)-(S)-alpha-(2-chlorophenyl)-6,7-dihydrothieno[3,2-c]pyridine-5(4H)-acetic acid methyl ester (Clopidogrel, Formula I) as hydrogen sulfate salt was dissolved in methanol (1500 ml, 3 v) to get a clear solution. This solution was then concentrated to remove methanol 1000 ml (2 v) so as to maintain the methanol volume in the reaction mixture 500 ml (1 v) at below 40° C. under 500-600 mm vacuum. This solution was cooled to room temperature and ethyl acetate (500 ml, 1 v) was added. A clear solution was stirred at room temperature. After 1 hr slight turbidity was observed and stirring was continued for total 4 hrs. The first lot solid was filtered and washed with 25-ml acetone. The mother liquor was concentrated to dryness and to this residue 1500.0-ml acetone was added. This reaction mixture was further stirred at room temperature for 4 hrs. The second lot solid was filtered & washed with 20-25 ml of acetone. The material was dried at 40-45° C. for 3 hrs under 650-700 mm vacuum to furnish the final material. Further details are described in Table 3 as follows:

TABLE 3

| Isolated Material of Formula I as hydrogen | Yield | | Optical | Chiral HPLC Purity (%) of Formula I as hydrogen sulfate salt | |
|---|---|---|---|---|---|
| SN hydrogen sulfate salt | gm | % age | Rotation | S(+)Enantiomer | R(−)Enantiomer |
| 1. First Lot | 31.0 | 6.2 | +21.2° | 69.04 | 30.96 |
| 2. Second Lot | 448.0 | 89.6 | +56.2° | 99.84 | 00.16 |

Optical Rotation ($[a]_D^{20}$) of Formula I is checked as hydrogen sulfate salt with 2.0% concentration of MeOH.

Example-5

Preparation of Methyl-(+)-(S)-alpha-(2-chlorophenyl)-6,7-dihydrothieno[3,2-c]pyridine-5 (4H)-acetic acid methyl ester (Clopidogrel, Formula I) as hydrogen sulfate salt A solution of 15 gm of Methyl-(+)-(S)-alpha-(2-chlorophenyl)-6,7-dihydrothieno[3,2-c]pyridine-5(4H)-acetic acid methyl ester (Clopidogrel, Formula I) in a mixture of acetone (41.25 ml, 2.75 v) & Isopropylether (3.75 ml, 0.25 v) was cooled to 9-10° C. The first portion of conc. sulfuric acid (98%) (0.23 gm) was added at 9-10° C. under stirring. After complete addition of sulfuric acid the reaction mixture was heated to room temperature 25-30° C. and stirred for 3 hrs. After 3 hrs the first lot solid was filtered and washed with 10 ml of acetone. The mother liquor was again cooled to 0-5° C. and second portion of conc. sulfuric acid (98%) (4.43 gm) was added at 0-5° C. under stirring. After complete addition of conc. sulfuric acid, the reaction mixture was heated to room temperature 25-30° C. and stirred for 3 hrs. The separated second lot solid was filtered and washed with 3-5 ml of acetone & dried at 40-45° C. for 3 hrs under 650-700 mm vacuum to furnish the final material.

1. Optical Rotation ($[\alpha]_D^{20}$) of Formula II as HCl salt=+104° {used here to make Clopidogrel free base was checked with 1.0% concentration of MeOH}.
2. Optical Rotation ($[\alpha]_D^{20}$) of Formula I was checked as hydrogen sulfate salt with 2.0% concentration of MeOH.

The ratio of solvent mixture & two lots of $H_2SO_4$ are summarized in Table 4.

TABLE 4

| | Combination of Solvents | | Ratio of solvent | | Conc. H₂SO₄ in gm | | | |
| | | | | | Percentage | | Amount | |
| SN | I Solvent | II Solvent | I Solvent | II Solvent | I Lot | II Lot | I Lot | II Lot |
|---|---|---|---|---|---|---|---|---|
| 1. | Acetone | Isopropyl ether | 2.75 | 0.25 | 5 | 95 | 0.23 | 4.40 |

The yields of both lots of Clopidogrel $H_2SO_4$ and their purities are summarized in Table 5.

TABLE 5

| | | | Result of Formula I as hydrogen sulfate salt | | | | |
| | Combination of Solvents | | Optical Rotation in 2% in methanol | | Yield (gm) | | Chiral HPLC |
| SN | I Solvent | II Solvent | I Lot | II Lot | I Lot | II Lot | II Lot |
|---|---|---|---|---|---|---|---|
| 1. | Acetone | Isopropyl ether | +16.4° | +55.6° | 0.80 | 16.4 | 99.21 |

Example-6

Preparation of Methyl-(+)-(S)-alpha-(2-chlorophenyl)-6,7-dihydrothieno[3,2-c]pyridine-5(4H)-acetic acid methyl ester (Clopidogrel, Formula I) as hydrogen sulfate salt A solution of 15 gm of Methyl-(+)-(S)-alpha-(2-chlorophenyl)-6,7-dihydrothieno[3,2-c]pyridine-5(4H)-acetic acid methyl ester (Clopidogrel, Formula I) in a mixture of methylethylketone (41.25 ml, 2.75 v) & isopropylether (3.75 ml, 0.25 v) was cooled to 9-1° C. The first portion of conc. sulfuric acid (98%) (0.23 gm) was added at 9-10° C. under stirring. After complete addition of sulfuric acid the reaction mixture was heated to room temperature 25-30° C. and stirred for 3 hrs. After 3 hrs the first lot solid was filtered and washed with 2 ml of methylethylketone. The mother liquor was again cooled to 0-5° C. and second portion of conc. sulfuric acid (98%) (4.43 gm) was added at 0-5° C. under stirring. After complete addition of conc. sulfuric acid, the reaction mixture was heated to room temperature 25-30° C. and stirred for 3 hrs. The separated second lot solid was filtered and washed with 3-5 ml of methylethylketone & 5 ml of isopropylether & dried at 40-45° C. for 3 hrs under 650-700 mm vacuum to furnish the final material.

1. Optical Rotation ($[\alpha]_D^{20}$) of Formula II as HCl salt=+104° {used here to make Clopidogrel free base was checked with 1.0% concentration of MeOH}.
2. Optical Rotation ($[\alpha]_D^{20}$) of Formula I was checked as hydrogen sulfate salt with 2.0% concentration of MeOH.

The ratio of solvent mixture & two lots of $H_2SO_4$ are summarized in Table 6.

TABLE 6

| | Combination of Solvents | | Ratio of solvent | | Conc. H₂SO₄ in gm | | | |
| | | | | | Percentage | | Amount | |
| SN | I Solvent | II Solvent | I Solvent | II Solvent | I Lot | II Lot | I Lot | II Lot |
|---|---|---|---|---|---|---|---|---|
| 1. | Methyl ethyl Ketone | Isopropyl ether | 2.75 | 0.25 | 5 | 95 | 0.23 | 4.41 |

The yields of both lots of Clopidogrel $H_2SO_4$ and their purities are summarized in Table 7.

TABLE 7

| | | | Result of Formula I as hydrogen sulfate salt | | | | |
| | Combination of Solvents | | Optical Rotation | | Yield (gm) | | Chiral HPLC |
| SN | I Solvent | II Solvent | I Lot | II Lot | I Lot | II Lot | II Lot |
|---|---|---|---|---|---|---|---|
| 1. | Methyl ethyl Ketone | Isopropyl ether | +30.8° | +55.4° | 1.0 | 16.2 | 99.12 |

Example-7

Preparation of Methyl-(+)-(S)-alpha-(2-chlorophenyl)-6,7-dihydrothieno[3,2-c]pyridine-5(4H)-acetic acid methyl ester (Clopidogrel, Formula I) as hydrogen sulfate salt A solution of 15 gm of Methyl-(+)-(S)-alpha-(2-chlorophenyl)-6,7-dihydrothieno[3,2-c]pyridine-5(4H)-acetic acid methyl ester (Clopidogrel, Formula I) in a mixture of methylethylketone (42 ml, 2.75 v) & isopropylalcohol (3.0 ml, 0.20 v) was cooled to 9-10° C. The first portion of conc. sulfuric acid (98%) (0.42 gm) was added at 9-10° C. under stirring. After complete addition of sulfuric acid the reaction mixture was heated to room temperature 25-30° C. and stirred for 3 hrs. After 3 hrs the first lot solid was filtered and washed with 2 ml of methylethylketone. The mother liquor was again cooled to 0-5° C. and second portion of conc. sulfuric acid (98%) (4.24 gm) was added at 0-5° C. under stirring. After complete addition of conc. sulfuric acid, the reaction mixture was heated to room temperature 25-30° C. and stirred for 3 hrs. The separated second lot solid was filtered and washed with 3-5 ml of methylethylketone & dried at 40-45° C. for 3 hrs under 650-700 mm vacuum to furnish the final material.

1. Optical Rotation ($[\alpha]_D^{20}$) of Formula II as HCl salt=+102° {used here to make Clopidogrel free base was checked with 1.0% concentration of MeOH}.
2. Optical Rotation ($[\alpha]_D^{20}$) of Formula I was checked as hydrogen sulfate salt with 2.0% concentration of MeOH.

The ratio of solvent mixture & two lots of $H_2SO_4$ are summarized in Table 8.

TABLE 8

| | | | | | Conc. $H_2SO_4$ in gm | |
|---|---|---|---|---|---|---|
| Combination of Solvents | | Ratio of solvent | | Percentage | Amount | |
| SN I Solvent | II Solvent | I Solvent | II Solvent | I Lot II Lot | I Lot | II Lot |
| 1. Methyl ethyl Ketone | Isopropyl alcohol | 2.75 | 0.25 | 9  91 | 0.41 | 4.23 |

The yields of both lots of Clopidogrel $H_2SO_4$ and their purities are summarized in Table 9.

TABLE 9

| | | Result of Formula I as hydrogen sulfate salt | | | | |
|---|---|---|---|---|---|---|
| Combination of Solvents | | Optical Rotation in | | Yield (gm) | | Chiral HPLC |
| SN I Solvent | II Solvent | I Lot | II Lot | I Lot | II Lot | II Lot |
| 1. Methyl ethyl Ketone | Isopropyl alcohol | +28.1° | +55.9° | 1.6 | 15.3 | 99.44 |

The one volume of S(+)clopidogrel free base of Formula I as referred herein means one gm of S(+)clopidogrel free base of Formula I, because S(+)clopidogrel free base of Formula I, being oily in nature, is measured in weight units.

The optical rotation [specific rotation] referred herein was measured by polarimeter—Perkin Elmer 341 and the chiral purity referred herein was measured by HPLC—Perkin Elmer 785A by analytical method as per USP.

It may be noted that the word about appearing before a value is intended to include permissible practical errors.

It will be obvious to the persons skilled in the art after referring to the forgoing description and the forgoing examples and their findings that the various modifications are possible without deviating from the intended scope of the present invention. Accordingly, in one embodiment of the present invention such modifications are also included within the scope of the present invention.

The invention claimed is:

1. A process for preparation of Methyl-(+)-(S)-alpha-(2-chlorophenyl)-6,7-dihydrothieno[3,2-c]pyridine-5(4H)-acetic acid methyl ester as free base [S(+)clopidogrel free base] of Formula-I,

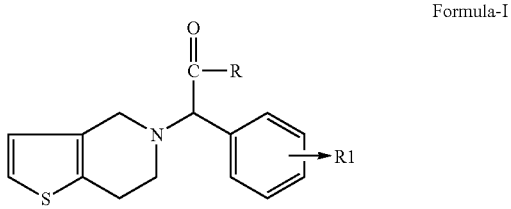

Formula-I comprising following steps:

a) reacting an aqueous solution of a S(+)enantiomer of compound of Formula-II as hydrochloride salt with paraformaldehyde and catalytic amount of hydrochloric acid;

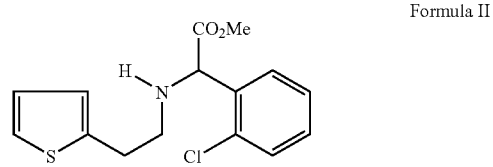

Formula II b) heating the reaction mixture of step a);
c) separating out the aqueous layer from the sticky mass;

d) extracting the S(+)clopidogrel free base from the aqueous layer obtained in step c) with petroleum ether or hexane while maintaining the pH varying between 2 to 3;

e) repeating the step d) while maintaining the said pH varying between 2 to 3 of the aqueous layer; and f) concentrating the combined organic layers obtained in steps d) and e) to result in S(+)clopidogrel free base in chemical purity, as checked by Gas Chromatography, of 99.5% or more and yield of 80% or more.

2. A process as claimed in claim 1, wherein said pH varying between 2 to 3 of the aqueous layer is maintained by addition of a base.

3. A process as claimed in claim 2, wherein said base is ammonia solution.

4. A process as claimed in claim 1, wherein the pH of the aqueous layer is maintained between 2.2 to 2.6.

5. A process as claimed in claim 1, wherein catalytic amount of hydrochloric acid is added to a stirred aqueous solution of compound of Formula-II either along with paraformaldehyde or immediately after addition of paraformaldehyde.

6. A process as claimed in claim 1, wherein said reaction mixture in step-b) is heated at a temperature of 75-85 degree C.

7. A process as claimed in claim 1, wherein paraformaldehyde is taken in an amount of 12 to 18% of the amount of S(+)enantiomer of compound of Formula-II as hydrochloride salt.

8. A process as claimed in claim 5, wherein hydrochloric acid is taken in an amount of 0.1 to 0.5% of the amount of S(+)enantiomer of compound of Formula-II as hydrochloride salt.

9. A process as claimed in claim 1, wherein yield of S(+) clopidogrel free base is 85% or more.

10. A process for preparation of Methyl-(+)-(S)-alpha-(2-chlorophenyl)-6,7-dihydrothieno[3,2-c]pyridine-5(4H)-acetic acid methyl ester as hydrogen sulfate [S(+)clopidogrel hydrogen sulfate] of Formula-I,

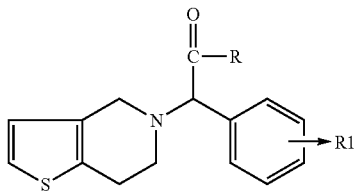

Formula-I comprising following steps:

a) reacting an aqueous solution of a S(+)enantiomer of compound of Formula-II as hydrochloride salt with paraformaldehyde and catalytic amount of hydrochloric acid;

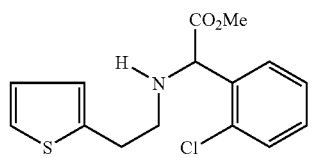

Formula II b) heating the reaction mixture of step a);
c) separating out the aqueous layer from the sticky mass;

d) extracting the S(+)clopidogrel free base from the aqueous layer obtained in step c) with petroleum ether or hexane while maintaining the pH varying between 2 to 3;

e) repeating the step d) while maintaining the said pH varying between 2 to 3 of the aqueous layer;

f) concentrating the combined organic layers obtained in steps d) and e) to result in S(+)clopidogrel free base of Formula I in chemical purity, as checked by Gas Chromatography, of 99.5% or more and yield of 80% or more;

g) stepwise reacting S(+)clopidogrel free base of Formula I obtained in step-f) with conc. sulfuric acid in presence of organic solvent to form S(+)clopidogrel hydrogen sulfate of Formula I, and h) stepwise separating out S(+)clopidogrel hydrogen sulfate of Formula I formed in step-g) from the reaction mass, wherein S(+)clopidogrel free base is reacted with conc. sulfuric acid in at least two steps, and the first portion of conc. sulfuric acid is 5% to 30% and second portion is 95% to 70%, and wherein organic solvent is a mixture of ketone and a solvent selected from group consisting of hydrocarbon, alcohol and ether.

11. A process as claimed in claim 10, wherein the organic solvent is a mixture of acetone and toluene.

12. A process as claimed in claim 10, wherein 2.2 to 2.8 volumes of ketone is taken for each volume of S(+)clopidogrel free base of Formula I.

13. A process as claimed in claim 10, wherein 0.2 to 0.8 volumes of hydrocarbon is taken for each volume of S(+) clopidogrel free base of Formula I.

14. A process as claimed in claim 10, wherein the ketone is methylethylketone.

15. A process as claimed in claim 10, wherein the organic solvent is a mixture of ketone and alcohol.

16. A process for preparation of Methyl-(+)-(S)-alpha-(2-chlorophenyl)-6,7-dihydrothieno[3,2-c]pyridine-5(4H)-acetic acid methyl ester as hydrogen sulfate [S(+)clopidogrel hydrogen sulfate] of Formula-I,

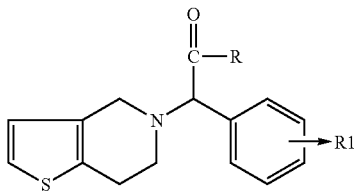

Formula-I comprising following steps:

a) reacting an aqueous solution of a S(+)enantiomer of compound of Formula-II as hydrochloride salt with paraformaldehyde and catalytic amount of hydrochloric acid;

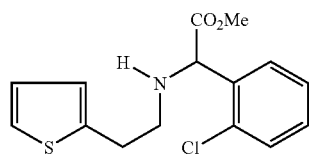

Formula II b) heating the reaction mixture of step a);
c) separating out the aqueous layer from the sticky mass;

d) extracting the S(+)clopidogrel free base from the aqueous layer obtained in step c) with petroleum ether or hexane while maintaining the pH varying between 2 to 3;
e) repeating the step d) while the said pH varg between 2 to 3 of the aqueous layer;
f) concentrating the combined organic layers obtained in steps d) and e) to result in S(+)clopidogrel free base of Formula I in chemical purity, as checked by Gas Chromatography, of 99.5% or more and yield of 80% or more;
g) reacting S(+)clopidogrel free base of Formula I obtained in step-f) with conc. sulfuric acid in one lot in presence of organic solvent to form S(+)clopidogrel hydrogen sulfate of Formula I, and
h) stepwise separating out S(+)clopidogrel hydrogen sulfate of Formula I formed in step-g) from the reaction mass, and wherein organic solvent is a mixture of methanol and ethyl acetate.

17. A process as claimed in claim 16, wherein one volume of each of methanol and ethyl acetate are taken for one volume of S(+)clopidogrel free base of Formula I.

18. A process as claimed in claim 16, wherein methanol and ethyl acetate are taken in a ratio varying from 1:1 to 1:2.

19. A process as claimed in claim 10, further comprising steps of:
   i) dissolving S(+)clopidogrel hydrogen sulfate of Formula I of lower optical rotation obtained in step-h) of claim 10 in an organic solvent to have a clear solution,
   j) concentrating the clear solution of step-i) and adding about 1 volume of ethyl acetate to precipitate out undesired clopidogrel hydrogen sulfate and chemical impurities which are separated out as first lot, and
   k) followed by further concentration to dryness to give S(+)clopidogrel hydrogen sulfate of Formula I of optical rotation of 55.0 degree or more and chiral purity of 99.0% or more as second lot on addition of organic solvent.

20. A process as claimed in claim 19, wherein said organic solvent is selected from group consisting of methanol and acetone.

21. A process as claimed in claim 19, wherein optical rotation of S(+)clopidogrel hydrogen sulfate of Formula I obtained in second lot is 55.5 degree or more with chiral purity of 99.5% or more.

22. A process as claimed in claim 16, further comprising steps of:
   i) dissolving S(+)clopidogrel hydrogen sulfate of Formula I of lower optical rotation obtained in step-h) in an organic solvent to have a clear solution,
   j) concentrating the clear solution of step-i) and adding about 1 volume of ethyl acetate to precipitate out undesired clopidogrel hydrogen sulfate and chemical impurities which are separated out as first lot, and
   k) followed by further concentration to dryness to give S(+)clopidogrel hydrogen sulfate of Formula I of optical rotation of 55.0 degree or more and chiral purity of 99.0% or more as second lot on addition of organic solvent.

23. A process as claimed in claim 22, wherein said organic solvent is selected from group consisting of methanol and acetone.

24. A process as claimed in claim 22, wherein optical rotation of S(+)clopidogrel hydrogen sulfate of Formula I obtained in second lot is 55.5 degree or more with chiral purity of 99.5% or more.

25. A process as claimed in claim 1, wherein said reaction mixture in step-b) is heated at a temperature of 75-80 degree C.

26. A process as claimed in claim 15, wherein the alcohol is isopropyl alcohol.

27. A process as claimed in claim 10, wherein the organic solvent is a mixture of ketone and ether.

28. A process as claimed in claim 27, wherein ether is isopropylether.

* * * * *

UNITED STATES PATENT AND TRADEMARK OFFICE
CERTIFICATE OF CORRECTION

| | | |
|---|---|---|
| PATENT NO. | : 8,063,217 B2 | Page 1 of 1 |
| APPLICATION NO. | : 11/993249 | |
| DATED | : November 22, 2011 | |
| INVENTOR(S) | : Srivastava et al. | |

It is certified that error appears in the above-identified patent and that said Letters Patent is hereby corrected as shown below:

On the title page item (30),
"Jul. 6, 2006 (IN) ............. 836/MUM/2006" should read
-- Jul. 6, 2006 (IN) ............... 836/MUM/2005 --

Signed and Sealed this
Nineteenth Day of June, 2012

David J. Kappos
*Director of the United States Patent and Trademark Office*